United States Patent
Etienne

(10) Patent No.: US 9,578,827 B2
(45) Date of Patent: Feb. 28, 2017

(54) WHEAT CULTIVAR TW419-052 AND COMPOSITIONS AND METHODS OF USING THE SAME

(71) Applicant: Agrigenetics, Inc., Indianapolis, IN (US)

(72) Inventor: Mark J. Etienne, Forest (CA)

(73) Assignee: Agrigenetics, Inc., Indianapolis, IN (US)

( * ) Notice: Subject to any disclaimer, the term of this patent is extended or adjusted under 35 U.S.C. 154(b) by 0 days.

(21) Appl. No.: 14/339,502

(22) Filed: Jul. 24, 2014

(65) Prior Publication Data

US 2015/0040262 A1 Feb. 5, 2015

Related U.S. Application Data

(60) Provisional application No. 61/861,141, filed on Aug. 1, 2013.

(51) Int. Cl.
*A01H 5/10* (2006.01)
(52) U.S. Cl.
CPC ..................................... *A01H 5/10* (2013.01)

(58) Field of Classification Search
None
See application file for complete search history.

(56) References Cited

U.S. PATENT DOCUMENTS 7,598,442 B2 * 10/2009 Laskar ..................... A01H 5/10
435/410

* cited by examiner

*Primary Examiner* — Cynthia Collins
(74) *Attorney, Agent, or Firm* — Marcos P. Rivas

(57) ABSTRACT

A wheat cultivar designated TW419-052 is disclosed. The invention relates to the seeds and plants of wheat cultivar TW419-052, and to methods for producing wheat seeds and plants by crossing wheat cultivar TW419-052 with itself or another wheat cultivar or wheat plant not designated a cultivar. The invention also relates to methods for producing seeds and plants of wheat cultivar TW419-052 containing in its genetic material one or more transgenes and to the transgenic wheat plants and plant parts produced by those methods. The invention also relates to methods for producing seeds and plants by mutagenesis of wheat cultivar TW419-052. The invention also relates to hybrid wheat seeds and plants produced by crossing wheat cultivar TW419-052 with another wheat cultivar.

19 Claims, No Drawings

WHEAT CULTIVAR TW419-052 AND COMPOSITIONS AND METHODS OF USING THE SAME

CROSS REFERENCE TO RELATED APPLICATIONS

The present application claims priority to U.S. Provisional Application No. 61/861,141 filed on Aug. 1, 2013, the entire contents of which are incorporated herein by reference.

FIELD OF THE DISCLOSURE

This invention relates generally to developing a wheat (*Triticum aestivum* L.) cultivar, and more specifically to a wheat cultivar designated TW419-052 and uses thereof.

BACKGROUND

Wheat is an important crop as a food staple and nutritional agent, and has been domesticated for about 10,000 years. In 2007, world production of wheat was 607 million tons, which makes wheat the third most-produced cereal after maize and rice. Wheat grain is a staple food used to make flour for leavened, flat, and steamed breads, biscuits, cookies, cakes, breakfast cereal, pasta, noodles, couscous, and for fermentation to make beer, alcohol, vodka, or biofuels. Wheat is also planted to a limited extent as a feed and/or forage crop for livestock and as a construction material for roofing thatch.

Wheat is divided into five main market classes, which includes the common wheat (*Triticum aestivum* L.) classes: hard red winter, hard red spring, soft red winter, soft and hard white, and durum (*Triticum turgidum* L.). Common wheats are used in numerous food products, such as bread, cookies, cakes, crackers, and noodles. In general, the hard wheat classes are milled into flour used for breads and the soft wheat classes are milled into flour used in products, such as pastries, crackers, breakfast cereals, and soup thickeners. Wheat starch can be used in the food and paper industries, as laundry starches, and in other products.

White wheat contains the same healthy levels of whole grain fiber that red wheat does, but does not have as strong a flavor or dark color. White wheat may be actually golden in color. It tastes sweeter and is lighter than its hard red wheat counterparts. White wheat is planted like red wheat, grows like red wheat, and produces similar yields to red wheat. The difference between red and white wheat is the color of the seed coat. The differences between hard and soft white wheat are found mainly in the end products for which they are used; soft white has a lower protein level than hard white. Thus, soft white wheat is used mainly for bakery products other than bread. Examples include pastries, cakes, and cookies. Soft white wheat is also used for cereals, flat breads, and crackers.

Hard white wheat can be used for the same products as hard red wheat. Hard white wheat is used, for example, in whole-wheat and high-extraction flour applications. Bakers like it because hard white wheats are excellent for use in the bread making industry. Because it has a naturally sweeter flavor, bakers can use less sweeteners. International customers prefer it for at least two reasons: 1) higher extraction of white wheat flour while maintaining its bright white color; and 2) most white wheat gives better color stability in Asian wet noodles. Hard white wheat can be used as an ingredient for all yeast breads, Artisan breads, Asian noodles, tortillas, pizza crusts, breadsticks, flatbreads, quick breads, and more.

In order to fulfill their demands, flour millers must choose among available wheat cultivars grown in different regions, depending upon soil and climate characteristics, and having different milling properties. For example, soft red winter wheats are typically grown in Ohio, Indiana, and areas of the Southeastern U.S. Meanwhile, soft white wheats are generally grown in the Pacific Northwest and Michigan. Hard red winter wheats are primarily grown in Kansas, Nebraska, Oklahoma, and Texas. Hard wheats typically have higher gluten strength properties that are better suited for bread baking than soft wheats. Therefore, commercial bread bakers are generally biased in favor of flours made primarily from hard wheat cultivars, and these cultivars are demanded by millers accordingly.

Currently, red wheat is more readily available in the United States than white wheat. Production of hard white wheat in the United States was on less than 2 million acres in 2006. Hard red wheats are characterized by a relatively strong wheat flavor that consumers may not want for whole wheat bread products. Red wheat also has a distinctive bitter taste due to the tannins and phenolic compounds in the bran that many consumers find unpleasant, and which is offset in the final baking product by the presence of expensive sweeteners. Moreover, red wheats will have a red color in the intact wheat kernel and its outer layers. The distinct red hue of whole wheat flour milled from hard red wheat cultivars may be problematic for bread products like whole wheat croissants and Danish rolls that consumers typically associate with a white hue. Furthermore, bran separated from hard red wheat cultivars is generally only suitable for animal feeds, and therefore is less valuable to the miller than brans derived from white wheat cultivars that may be used in breakfast cereals and other bran products consumed by humans. Red wheat also may have lower milling performance compared to white wheat, because a significantly higher extraction rate may be used with white wheat without sacrificing flour color.

Wheat breeders continually develop stable, high yielding wheat cultivars that are agronomically sound and have good grain quality for its intended use. To accomplish this goal, the wheat breeder must select and develop wheat plants that have the traits that result in superior cultivars. These selection processes, which ultimately lead to the marketing and distribution of the wheat cultivar, can take many years from the time the first cross is made. Development of new wheat cultivars is therefore a time-consuming process that requires precise forward planning, efficient use of resources, and a minimum of changes in direction.

Choice of breeding or selection methods depends on the mode of plant reproduction, the heritability of the trait(s) being improved, and the type of cultivar used commercially; e.g., $F_1$ hybrid cultivar, pure-line cultivar, etc. For highly heritable traits, a choice of superior individual plants evaluated at a single location can be effective, whereas for traits with low heritability, selection may be based on mean values obtained from replicated evaluations of families of related plants. Popular selection methods commonly include pedigree selection, modified pedigree selection, mass selection, and recurrent selection.

Pedigree breeding can be used for the improvement of self-pollinating crops. Two parents that possess favorable, complementary traits are crossed to produce an $F_1$. An $F_2$ population is produced by selfing or sibbing one or several $F_1$ so selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_5$, $F_6$ and $F_7$), the best lines or mixtures of phenotypically similar lines are tested for potential release as new cultivars.

Backcross breeding is used to transfer genes for simply inherited, qualitative traits from a donor parent into a desirable homozygous cultivar that is utilized as the recurrent parent. The source of the traits to be transferred is called the donor parent. After the initial cross, individuals possessing the desired trait or traits of the donor parent are selected and then repeatedly crossed (backcrossed) to the recurrent parent. The resulting plant is expected to have the attributes of the recurrent parent (e.g., cultivar) plus the desirable trait or traits transferred from the donor parent. This approach has been used extensively for breeding disease resistant varieties.

Another breeding method that can be utilized is single-seed descent. This procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed. In a multiple-seed procedure, wheat breeders commonly harvest one or more spikes (heads) from each plant in a population and thresh them together to form a bulk. Part of the bulk is used to plant the next generation and part is put in reserve. The procedure has been referred to as modified single-seed descent. The multiple-seed procedure has been used to save labor at harvest. It is considerably faster to thresh spikes with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Bulk breeding can also be used. In the bulk breeding method an F2 population is grown. The seed from the populations is harvested in bulk and a sample of the seed is used to make a planting the next season. This cycle can be repeated several times. In general when individual plants are expected to have a high degree of homozygosity, individual plants are selected, tested, and increased for possible use as a variety.

The production of doubled haploids can also be used for the development of homozygous lines in the breeding program. Doubled haploids are produced by the doubling of a set of chromosomes (1N) from a heterozygous plant to produce a completely homozygous individual. This can be advantageous because the process omits the generations of selfing needed to obtain a homogygous plant from a heterozygous source. Various methodologies of making doubled haploid plants in wheat have been developed.

Although most commercial wheat production is from pure-line inbred cultivars, hybrid wheat is also grown. Hybrid wheat is produced with the help of cytoplasmic male sterility, nuclear genetic male sterility, or chemicals. Various combinations of these three male-sterility systems have been used in the production of hybrid wheat.

SUMMARY OF THE INVENTION

The following embodiments are described in conjunction with systems, tools and methods that are meant to be exemplary and illustrative, and not limiting in scope. The present technology provides seeds of soft red winter wheat cultivar designated TW419-052, representative seed of cultivar TW419-052 deposited under American Type Culture Collection (ATCC) Patent Deposit Designation No. PTA-13626. The present technology can also provide compositions and methods that include use, or operate on, or are derived from TW419-052. Such technology includes seeds of TW419-052, whole plants and portions of plants of TW419-052, and methods for producing a wheat plant by crossing FW419-052 with another wheat plant. These methods further include developing other wheat cultivars or breeding lines derived from TW419-052 and compositions that include the wheat cultivars or breeding lines produced by those methods. Creation of variants, by mutagenesis or transformation of TW419-052, is also provided. The present compositions and methods can also relate to transgenic backcross conversions of TW419-052. This invention also relates to methods for developing other wheat varieties or breeding lines derived from wheat variety TW419-052 and to wheat varieties or breeding lines produced by those methods. Products include flour and other refined or isolated materials derived from cultivar TW419-052. For example, these include edible products such as baked goods, cereals, pastas, beverages, livestock feeds, energy products such as biofuels, and further include non-edible products such as wheat straw and construction materials produced from TW419-052.

Other embodiments can include methods for producing $F_1$ wheat seeds comprising crossing a wheat plant of the invention with a different wheat plant and harvesting the resulting $F_1$ wheat seed. Additional embodiments can include a method of producing a male-sterile wheat plant comprising transforming the wheat plant with a nucleic-acid molecule that confers male sterility. Yet another embodiment can include methods of producing an herbicide or insect resistant wheat plant comprising transforming the wheat plant with a transgene that confers herbicide or insect resistance.

DETAILED DESCRIPTION

The following description of the invention is merely exemplary in nature of the subject matter, manufacture, and use of the invention, and is not intended to limit the scope, application, or uses of the specific invention claimed in this application or in such other applications as may be filed claiming priority to this application, or patents issuing therefrom. The following definitions and non-limiting guidelines must be considered in reviewing the description of the technology set forth herein.

A wheat cultivar or variety needs to be highly homogeneous, homozygous and reproducible to be useful as a commercial cultivar. Throughout this application cultivar and variety may be used interchangeably. There are many analytical methods available to determine the homozygotic stability, phenotypic stability, and identity of these varieties.

The oldest and most traditional method of analysis is the observation of phenotypic traits. The data is usually collected in field experiments over the life of the wheat plants to be examined. Phenotypic characteristics most often observed are for traits such as seed yield, head configuration, glume configuration, seed configuration, lodging resistance, disease resistance, maturity, etc.

In addition to phenotypic observations, the genotype of a plant can also be examined. There are many laboratory-based techniques available for the analysis, comparison and characterization of plant genotype; among these are Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). Gel electrophoresis is particularly useful in wheat. Wheat cultivar identification is possible through electrophoresis of gliadin, glutenin, albumin and globulin, and total protein extracts (Bietz, J. A., pp. 216-228, "Genetic and Biochemical Studies of Nonenzymatic Endosperm Proteins" In Wheat and Wheat Improvement, ed. E. G. Heyne, 1987).

The cultivar of the invention has shown uniformity and stability for all traits, as described in the following cultivar description information. It has been self-pollinated a sufficient number of generations, with careful attention to uniformity of plant type to ensure homozygosity and phenotypic stability. The line has been increased with continued observation for uniformity.

Molecular markers can be used to confirm such cultivar. These include techniques such as Starch Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs) may be used in plant breeding methods. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program (Openshaw et al. Marker-assisted Selection in Backcross Breeding. In: Proceedings Symposium of the Analysis of Molecular Marker Data, 5-6 Aug. 1994, pp. 41-43. Crop Science Society of America, Corvallis, Oreg.). The use of molecular markers in the selection process is often called Genetic Marker Enhanced Selection.

Wheat cultivar TW419-052 is a soft red winter wheat. Cultivar TW419-052 demonstrates outstanding yield potential, very good overall disease and *Fusarium* package, very good winter hardiness, and very good pastry characteristics. Cultivar TW419-052 is particularly adapted to the northeastern United States and eastern Canada.

Wheat cultivar TW419-052, being substantially homozygous, can be reproduced by planting seeds of the line, growing the resulting wheat plants under self-pollinating or sib-pollinating conditions, and harvesting the resulting seed, using techniques familiar to the agricultural arts.

Definitions of Plant Characteristics

In order to facilitate discussion of the various embodiments of the invention, the following explanations of specific terms are provided:

Allele. Any of one or more alternative forms of a gene, all of which relate to one protein, trait, or characteristic. In a diploid cell or organism, the two alleles of a given gene occupy corresponding loci on the homologous chromosomes.

Awn. The elongated needlelike appendages on the flower- and seed-bearing "head" at the top of the cereal grain plant (e.g., wheat, common wheat, rye). Awnletted means having short awns (awnlets) and apically awnletted means the awnlets are only on the upper (apical) portion of the spike.

Awn attitude. When present, the orientation of awns; visually determined as Appressed or Spreading relative to the spike.

Awn color. When present, the color of the awns; visually determined to be White, Light Brown, Brown, or Black.

Awn length in relation to spike. When present, the relative length of the awns compared to the length of the spike to which they are attached; visually determined to be Shorter, Equal, or Longer than the spike.

Backcrossing. The process of introducing a gene or trait from a donor parent by crossing it to a recurrent parent, then repeatedly crossing progeny from each of several generations to the recurrent parent to recover a high proportion of the recurrent-parent genotype as well as the introduced gene or trait.

Barley Yellow Dwarf Virus. A disease of barley, oats, wheat, maize, triticale, and rice characterized by a yellowing or reddening of leaves, stunting, an upright posture of thickened stiff leaves, reduced root growth, and delayed (or no) heading. Caused by a single-stranded RNA virus of the genus, Luteovirus. In ratings on a scale of 0 to 9, 0 indicates no leaf discoloration or stunting, 1 indicates a trace of discoloration, 2 indicates a resistant reaction, 3 a moderately susceptible reaction, 4 to 8 increasing degrees of susceptibility, and 9 indicates the plants are dead because of the infection.

Cell. Includes a plant cell, whether isolated in tissue culture or incorporated in a plant or plant part.

Chaff color at maturity. The color of the dry protective casings of the seeds of cereal grain; visually determined as White, Yellow, Light Brown, Brown, Red, Purple, or Other Specified.

Coleoptile: anthocyanin coloration. The intensity of anthocyanin coloration in wheat coleoptiles 2 to 6 days after germination; visually determined to be Absent, Reddish, Purple, or Mixed.

Color of lower leaf blade. A description of the color of the lower leaf blade; visually determined to be Light Green, Medium Green, Dark Green, or Blue Green.

Culm. A stem of a wheat plant.

Culm shape of neck at maturity. The shape of the culm at maturity; visually determined to be Straight or Curved.

Culm waxiness of upper internode. The degree of waxiness along the culm; visually determined to be Absent, Slight, or Pronounced.

Culm pubescence of upper internode. The small hairs covering the culm; visually determined to be Glabrous, Slightly Pubescent, or Strongly Pubescent.

Deoxynivalenol (DON). Commonly referred to as vomitoxin, DON is a mycotoxin that may be produced in wheat and barley grain infected by *Fusarium* head blight (FHB) or scab. DON is measured in parts-per-million (PPM) using gas chromatography mass spectrometry on grain samples harvested from a screening nursery.

Disease Resistance. The ability of plants to restrict the activities of a specified pest, such as an insect, fungus, virus, or bacterium.

Disease Tolerance. The ability of plants to endure a specified pest (such as an insect, fungus, virus or bacterium) or an adverse environmental condition and still perform and produce in spite of this disorder.

Drought tolerance. The relative ability of the wheat plant to develop and yield grain in dry conditions; visually determined to be Not Tested, Poor, Fair, or Good.

Embryo (germ). The tissue contained within a mature seed that develops into the plant upon germination.

Flag leaf. The last leaf produced upon the culm.

Flag-leaf attitude. The angle of the flag leaf relative to the culm; visually determined to be Drooping, Intermediate, or Upright.

Flag-leaf auricle. Clasping appendage located at the junction of a flag-leaf sheath and the blade; hooks the sheath to the stem.

Flag-leaf auricles anthocyanin coloration. Visually determined to be Absent or Present.

Flag-leaf auricles pubescence of margins. A description of hairs on the margin of the flag-leaf auricle; visually determined to be Glabrous, Slightly Pubescent, or Strongly Pubescent.

Flag-leaf color. A description of the color of the flag leaf; visually determined to be Light Green, Medium Green, Dark Green, or Blue Green.

Flag-leaf curvature. A description of the shape of the flag leaf; visually determined to be Rectilinear, Slightly Recurved, Recurved, Strongly Recurved, or Very Strongly Recurved.

Flag-leaf length. The length of the flag leaf; visually determined to be Short, Medium, or Long.

Flag-leaf pubescence of blade. A description of hairs (trichomes) on the flag-leaf blade; visually determined to be Glabrous, Slightly Pubescent, or Strongly Pubescent.

Flag-leaf sheath pubescence. A description of hairs (trichomes) on the flag-leaf sheath; visually determined to be Glabrous, Slightly Pubescent, or Strongly Pubescent.

Flag-leaf sheath waxy bloom. A description of the waxiness on the surface of the flag-leaf sheath; visually determined to be Absent, Slight, or Pronounced.

Flag-leaf waxiness of lower side of blade. A description of the waxiness on the lower surface of the flag-leaf blade; visually determined to be Absent, Slight, or Pronounced.

Flag-leaf width. The width of the flag leaf; visually determined to be Narrow, Medium, or Wide.

Flour ash. Ash content after incineration is an indication of the yield and performance that can be expected during milling by indirectly revealing the amount of bran; expressed as a percentage of the initial sample weight on a common moisture basis such as 14%.

*Fusarium* head blight. A fungal disease caused by the fungus *Fusarium graminearum* characterized by tan or brown discoloration at the base of a floret with the spikelets of the head. As the infections progresses, the diseased spikelets become light tan or bleached and infected kernels are often shriveled, white, and chalky.

Gene. A segment of nucleic acid that codes for a protein. A gene can be introduced into a genome of a species from a different species using transformation.

Gene Converted (conversion). Plants that are developed by backcrossing, genetic engineering, or mutation wherein essentially all of the desired morphological and physiological characteristics of a variety are recovered in addition to the one or more traits (genes) transferred into the variety via backcrossing, genetic engineering, or mutation.

Genotype. The genetic constitution of a cell or organism.

Germ (embryo). The tissue contained within a mature seed that develops into the plant upon germination.

Germ (embryo) shape. The shape of the germ; visually determined as Round, Oval, or Other Specified.

Germ (embryo) size. The relative size of the germ; visually determined as Small, Midsize, or Large.

Glabrous. Free of hair or down, smooth.

Glaucosity (Glaucous). Covered with a greyish, bluish, or whitish waxy coating (bloom) that is easily rubbed off.

Glume. The dry protective casings (bracts) of the seed attached to the spikelet in grasses.

Grain ash. Ash content after incineration is an indication of the yield and performance that can be expected during milling by indirectly revealing the amount of bran; expressed as a percentage of the initial sample weight on a common moisture basis such as 14%.

Grain protein. Percentage protein content of the wheat grain at 13.5% moisture content; measured as nitrogen (x 5.7), freed by pyrolysis and subsequent combustion at high temperature in pure oxygen, quantified by thermal conductivity detection (AACC method 46-30).

Head (spike). The group of spikelets at the top of one plant stem.

Heading. The formation of the spike.

Juvenile growth habit. The angle formed by the outer leaves and the tillers at the 4-leaf stage assessed visually as Erect, Semi-erect, Intermediate, Semi-prostrate, or Prostrate.

Kernel cheek shape. The shape of the outer surface of a wheat kernel; visually determined to be Rounded, Slightly Angular, or Angular.

Kernel color. The outer color of the kernel; visually determined to be White, Light Red, Medium Red, Dark Red, Amber, Purple, or Other Specified.

Kernel crease depth. The depth of the crease in a wheat kernel; visually determined to be Shallow, Mid-deep, Deep, Pitted, or Other Specified.

Kernel crease width. The width of the crease in a wheat kernel; visually determined to be Narrow, Midwide, or Wide.

Kernel hardness. Average hardness of a sample of 300 kernels; measured by pressure force using the Single Kernel Characterization System (SKCS) and expressed as an index of −20 to 120.

Kernel length. The length of a wheat kernel; visually determined to be Short, Medium, or Long.

Kernel length of brush hairs. The length of the hairs (brush) on the end of a wheat kernel; visually determined to be Short, Medium, or Long.

Kernel phenol color reaction. The color of the seed; visually determined to be Ivory, Fawn, Light Brown, Brown, Black, or Mixed Specified assessed 4 hours after applying a 1% phenol solution to the outside of the kernel.

Kernel shape. The shape of the kernel; visually determined to be Oval, Ovate, Elliptical, or Other Specified.

Kernel size. The shape of the kernel; visually determined to be Small, Medium, Large, or Very Large.

Kernel size of brush. The overall size of the brush on the end of a wheat kernel; visually determined to be Small, Medium, or Large.

Kernel type. The type of kernel determined by its milling and baking properties to be Soft White, Soft Red, Hard White, Hard Red, or Other Specified.

Kernel Weight. The weight of individual kernels (also called seeds). In general, the weight in grams of one thousand kernels; also known as "1000 Kernel Weight".

Kernel width. The width of the kernel at its mid-section; visually determined to be Narrow, Medium, or Wide.

Leaf rust. A fungal disease caused by *Puccinia triticina* characterized by small brown pustules on the leaf blades in a random scatter distribution. Onset of the disease is slow but accelerated in temperatures above 15° C., making it a disease of the mature cereal plant in summer.

Linkage. Wherein two loci are physically located on the same chromosome.

Linkage Disequilibrium. Wherein alleles at two or more linked loci segregate from parent to offspring together at a frequency that is greater than expected if they segregated independently.

Locus (plural loci). A location on a chromosome that may genetically code for one or more traits such as male sterility, herbicide tolerance, insect resistance, disease resistance, waxy starch, modified fatty acid metabolism, modified phytic acid metabolism, modified carbohydrate metabolism, and modified protein metabolism. The trait may be, for example, conferred by a naturally occurring gene introduced into the genome of the variety by backcrossing, a natural or induced mutation, or a trans gene introduced through genetic transformation techniques.

Lodging. The bending or breakage of the plant stem, or the tilting of the plant; visually determined at harvest to be 0 to 9 where zero is no lodging and nine is complete lodging.

Lower glume. The outer glume on a spikelet.

Lower-glume beak length. The length of the tip (beak) of the lower glume on a spikelet; visually determined to be Short, Medium, or Long.

Lower-glume internal imprint. A clearly marked area caused by the pressure of the external surface of the lemma. They are distinguished as dark shadowy areas between the veins or nerves which run from the base of the glume to the beak and shoulder margins and are classified as Absent, Small, Medium, or Large.

Lower-glume length. The length of the lower glume; visually determined to be Short, Medium, or Long.

Lower-glume pubescence. A description of hairs on the lower glume extending from the beak along and across the lower glume; visually determined to be Glabrous, Slightly Pubescent, or Strongly Pubescent.

Lower-glume shape of beak. The shape of the tip (beak) of the lower glume; visually determined to be Obtuse, Acute, or Acuminate.

Lower-glume shape of shoulder. The shape of the shoulder on the lower glume; visually determined to be Wanting, Oblique, Rounded, Square, Elevated, Apiculate)

Lower-glume shoulder width. The width of the shoulder on the lower glume; visually determined to be Narrow, Medium, or Wide.

Lower-glume width. The width of the lower glume; visually determined to be Narrow, Medium, or Wide.

Maturity. The stage of plant growth at which the development of the kernels is complete.

Pedigree Distance. Relationship among generations based on their ancestral links as evidenced in pedigrees. May be measured by the distance of the pedigree from a given starting point in the ancestry.

Plant. An immature or mature whole plant, including a plant from which seed or grain or anthers have been removed. A seed or embryo that will produce the plant is also considered to be the plant.

Plant Height. The average height in inches centimeters of a group of plants, as measured from the ground to the tip of the head, excluding awns.

Plant Parts. Includes but is not limited to protoplasts, callus, leaves, stems, roots, root tips, anthers, pistils, seed, grain, pericarp, embryo, pollen, ovules, cotyledon, hypocotyl, spike, floret, awn, lemma, shoot, tissue, petiole, cells, meristematic cells and the like.

Powdery mildew. A fungal disease caused by *Erysiphe graminis* f. sp. *tritici*, it is characterized by a powdery white to gray fungal growth on leaves, stems, and heads during cool, humid weather. As the plant matures, the white powdery growth changes to a grey-brown color.

Pre-harvest sprouting. The premature germination of wheat seeds so that the embryo starts growing while still on the head in the field; visually determined to be Not Tested, Low, Medium, or High.

Progeny. An $F_1$ wheat plant produced from the cross of two wheat plants. Progeny further includes, but is not limited to, subsequent generational crosses with the recurrent parental line including $F_2$, $F_3$, $F_4$, $F_5$, $F_6$, $F_7$, $F_8$, and $F_9$.

Pubescence on blades of lower leaves. A description of hairs on the blades of lower leaves; visually determined to be Glabrous, Slightly Pubescent, or Strongly Pubescent.

Pubescence on sheaths of lower leaves. A description of hairs on the sheaths of lower leaves; visually determined to be Glabrous, Slightly Pubescent, or Strongly Pubescent.

Rachis. The main axis of the inflorescence, or spike, of wheat and other cereals, to which the spikelets are attached.

Rachis pubescence of margins. A description of hairs on the margins of the rachis; visually determined to be Glabrous, Slightly Pubescent, or Strongly Pubescent.

Regeneration. Regeneration refers to the development of a plant from tissue culture.

SDS sedimentation. A small scale chemical test for wheat flour which predicts gluten strength. Results are reported in millimeters. Values above 100 are typical for hard wheat and values below 100 are typical for soft wheat.

*Septoria tritici* leaf blotch. A disease of wheat, common wheat, and durum wheat characterized by irregularly shaped blotches that are at first yellow and then turn reddish brown with grayish brown dry centers, caused by the rust fungus, *Septoria tritici*. Also known as "speckled leaf blotch"

Shattering. The detachment of grain from the plant before harvest; visually determined to be Not Tested, Poor, Fair, or Good.

Spike (head). The cluster of grain found on a single stem of a wheat plant.

Spike attitude at maturity. The angle of the spike at maturity; visually determined to be Erect (upright to 30°), Inclined (30° to 90°), or Nodding (>90°).

Spike awnedness. The type of awn on the spike; visually determined to be Awnless, Apically Awnletted, Awnletted, or Awned.

Spike color at maturity. The color of the spike when the wheat plant has matured to dryness; visually determined to be White, Red to Brown, Purple to Black, or Other Specified.

Spike density. The density of the spikelets within the spike; visually determined to be Lax, Medium, or Dense.

Spike length excluding awns. The relative length of the spike, excluding awns; visually determined on the first tiller to be Short, Medium, or Long.

Spike shape. The shape of the spike; visually determined to be Tapering, Oblong, Clavate, Fusiform, or Other Specified.

Spike waxy bloom. The glaucosity of the spike; visually determined to be Absent, Slight, or Pronounced.

Spikelet. Small inflorescence bearing one or more florets (small flowers) along with a set of miniature bractlike leaves (glumes).

Stem color at maturity. The color of the stem when the wheat plant has matured to dryness; visually determined to be White, Yellow, Brown, Purple, or Other Specified.

Straw anthocyanin coloration at maturity. The relative amount of anthocyanin coloration in the straw at maturity; visually determined to be Absent, Medium, or Strong.

Straw pith. A description of the pith in a cross section of the stem halfway between the base of spike and the stem node below; visually determined to be Hollow, Thick Walled, or Solid.

Stripe Rust. A disease of wheat, common wheat, *durum* wheat, and barley characterized by elongated rows of yellow spores on the affected parts, caused by a rust fungus, *Puccinia striifarmis*. Resistance to this disease is scored on a scale that reflects the observed extent of the disease on the leaves of the plant. In ratings on a scale of 0 to 9, 0 indicates no lesions or production of spores, 1 indicates a trace of lesions or spores, 2 indicates a resistant reaction, 3 a moderately susceptible reaction, 4 to 8 increasing degrees of susceptibility, and 9 indicates the plants are dead because of the infection.

Test Weight. A measure of density that refers to the weight in pounds of grain kernels contained in one Avery bushel unit of volume. Avery bushel allows for grain compaction.

Tillering capacity at low densities. The relative amount of tillering produced at low planting densities; visually determined to be Low or High.

White wheat. Wheat varieties sufficiently white to allow discrimination from red wheats and meet grain classification standards. Whiteness may be measured either subjectively or objectively. A subjective minimum grain color standard for hard white wheat was established by the Federal Grain Inspection Service of USDA-GIPSA in 1990, when hard white wheat was officially recognized as a unique market class in the United States. The color standard was based on a grain sample for the hard white wheat cultivar "Klasic," produced in California. However, this color standard was waived in 1994 when numerous samples of "Klasic" were found with grain darker than the officially accepted standard. From 1994 to 1999, an interim classification procedure was used based on cultivar identity and production origin. The degree of "whiteness" of a given wheat may be empirically determined using near-infrared spectroscopy (NIRS), using the visible-near-infrared wavelength range (570-1098 nm). This wavelength range is the same used by protein-testing NIRS instruments at grain receiving and shipping points. The resulting "Minolta L* value" provide a measurement of whiteness; the higher the Minolta L* value, the greater is the degree of whiteness. Klasic standard white wheat was found to have an L* value of 41.35. Peterson et al. (2001) Euphytica 119:101-6.

Winter survival. Amount of survival of winter wheat; visually determined in the spring to be Poor, Fair, or Good.

Further reproduction of the wheat cultivar TW419-052 can occur by tissue culture and regeneration. Tissue culture of various tissues of wheat and regeneration of plants therefrom is well known and widely published. A review of various wheat tissue culture protocols can be found in "In Vitro Culture of Wheat and Genetic Transformation-Retrospect and Prospect" by Maheshwari et al. (Critical Reviews in Plant Sciences, 14(2):149-178, 1995). Thus, another aspect of this invention is to provide cells which upon growth and differentiation produce wheat plants capable of having the physiological and morphological characteristics of wheat cultivar TW419-052.

As used herein, the term plant parts includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

Numerous methods for plant transformation have been developed, including biological and physical, plant transformation protocols. See, for example, Mild et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

Various genetic elements can be introduced into the plant genome using transformation. These elements include but are not limited to genes; coding sequences; inducible, constitutive, and tissue specific promoters; enhancing sequences; and signal and targeting sequences.

A genetic trait which has been engineered into a particular wheat plant using transformation techniques, could be moved into another line using traditional breeding techniques that are well known in the plant breeding arts. For example, a backcrossing approach could be used to move a transgene from a transformed wheat plant to an elite wheat variety and the resulting progeny would comprise a transgene. As used herein, "crossing" can refer to a simple X by Y cross, or the process of backcrossing, depending on the context. The term "breeding cross" excludes the processes of selfing or sibbing.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114: 92-6 (1981).

By means of the present invention, agronomic genes can be expressed in plants of the present invention. More particularly, plants can be genetically engineered to express various phenotypes of interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance genes to engineer plants that are resistant to specific pathogen strains. See, for example, Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor I); Sumitani et al., *Biosci. Biotech. Biochem.* 57:1243 (1993) (nucleotide sequence of *Streptomyces nitrosporeus* .alpha.-amylase inhibitor); and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor); and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase; and Kawalleck et al., *Plant Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones; and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., *Plant Sci.* 89:43 (1993), of heterologous expression of a cecropin-β, lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988); and Mild et al., *Theor. Appl. Genet.* 80:449 (1990), respectively.

B. Glyphosate (resistance conferred by, e.g., mutant 5-enolpyruvylshikimate-3 -phosphate synthase (EPSPs) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (AC-Case inhibitor-encoding genes), See, for example, U.S. Pat. No. 4,940,835 to Shah, et al. and U.S. Pat. No. 6,248,876 to Barry et. al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al., DeGreef et al., *Bio/Technology* 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Accl-S1, Accl-S2 and Accl-S3 genes described by Marshall et al., *Theor. Appl. Genet.* 83:435 (1992). GAT genes capable of conferring glyphosate resistance are described in WO 2005012515 to Castle et al. Genes conferring resistance to 2,4-D, fop and pyridyloxy auxin herbicides are described in WO 2005107437 and U.S. patent application Ser. No. 11/587,893, both assigned to Dow AgroSciences LLC. Other representative genes include AAD1 and AAD12.

C. An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added or Quality Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content-1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene); Steinmetz et al., *Mol. Gen. Genet.* 20:220 (1985) (nucleotide sequence of *Bacillus subtilis* levansucrase gene); Pen et al., *Bio/Technology* 10:292 (1992) (production of transgenic plants that express *Bacillus licheniformis* α-amylase); Elliot et al., *Plant Molec. Biol.* 21:515 (1993) (nucleotide sequences of tomato invertase genes); Sogaard et al., *J. Biol. Chem.* 268:22480 (1993) (site-directed mutagenesis of barley α-amylase gene); and Fisher et al., *Plant Physiol.* 102:1045 (1993) (maize endosperm starch branching enzyme II).

D. Abiotic Stress Tolerance which includes resistance to non-biological sources of stress conferred by traits such as nitrogen utilization efficiency, altered nitrogen responsiveness, drought resistance cold, and salt resistance. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress.

E. Quality Traits. The wheat produced from the present invention can be used to make a wheat product with any quality or healthy trait. These can include soluble starch synthase(s) (SSS), starch branching enzyme(s) (SBE), starch de-branching enzyme(s) (DBE), arabinoxylans, fructans, beta glucans, etc. The physical properties of starch are strongly affected by the relative abundance of amylose and amylopectin, therefore SSSs, SBEs and DBEs play a key role in determining both starch quantity and quality.

SBE catalyses the formation of the α-1,6 linkages, creating branch points in the growing starch molecule, via hydrolysis of an α-1,4 linkage followed by reattachment of the released α-1,4-glucan chain to the same or another glucosyl chain. This reaction also provides a new non-reducing end for further elongation of the original α-1,4-glucan chain.

Multiple isoforms of starch branching enzyme have been described, biochemically, from a number of species including maize (Boyer and Preiss, 1978), rice (Nakamura et al., 1992), pea (Smith, 1988), potato (Khoshnoodi et al., 1993) and wheat (Morell et al., 1997). More recently, genomic and cDNA sequences for SBE have been characterised from several species including maize (Baba et al., 1991; Fisher et al., 1993; Gao et al. 1997) pea (Burton et al., 1995), potato (Kossmann et al., 1991), rice (Nakamura and Yamanouchi, 1992; Mizuno et al., 1993), *Arabidopsis* (Fisher et al., 1996), cassava (Salehuzzaman et al., 1992), and wheat (Rapellin et al., 1997, Nair et al., 1997, Rahman et al., 1997).

The wheat produced from the present invention can be used to make numerous products. The white wheat produced can confer high quality to 100% whole-wheat products. Whole-wheat products made from white wheat have a favorable appearance, when compared with similar products made from red wheat, since they have less pigmentation. Additionally, with fewer phenolic compounds and tannins in the bran, white wheat imparts a less bitter taste to the final product. Whole-wheat breads made with white wheat have a similar taste and appearance to bread made from refined red wheat flour. Therefore, substitution of white wheat for red wheat allows refining and bleaching of the flour to be reduced or eliminated, while still meeting consumers' expectations about the finished product's characteristics. Grain quality (milling properties) of wheat is very important for its use in baking. Important milling properties include relative hardness or softness, weight per bushel of wheat (test weight), siftability of the flour, break flour yield, middlings flour yield, total flour yield, flour ash content, and wheat-to-flour protein conversion. Processing quality for flour is also important. Quality characteristics for flour from soft wheats include low to medium-low protein content, low water absorption, production of large-diameter test cookies, and large volume cakes. Wheat glutenins and gliadins, which together confer the properties of elasticity and extensibility, play an important role in the grain quality. Changes in quality and quantity of these proteins change the end product for which the wheat can be used.

Introduction of a New Trait or Locus into TW419-052

Variety TW419-052 represents a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of TW419-052

A backcross conversion of TW419-052 occurs when DNA sequences are introduced through backcrossing (Fehr, 1993), with TW419-052 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Fehr, 1993). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance and herbicide resistance. In addition, an introgression site itself, such as an FRT site, Lox site or other site specific integration site, may be inserted by backcrossing and utilized for direct insertion of one or more genes of interest into a specific plant variety. In some embodiments of the invention, the number of loci that may be backcrossed into TW419-052 is at least 1, 2, 3, 4, 5, 6, 7, 8, 9 or 10. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, Breeding Field Crops, P. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

One process for adding or modifying a trait or locus in wheat variety TW419-052 comprises crossing TW419-052 plants grown from TW419-052 seed with plants of another wheat variety that comprise the desired trait or locus, selecting $F_1$ progeny plants that comprise the desired trait or locus to produce selected $F_1$ progeny plants, crossing the selected progeny plants with the TW419-052 plants to produce backcross progeny plants, selecting for backcross progeny plants that have the desired trait or locus and the morphological characteristics of wheat variety TW419-052 to produce selected backcross progeny plants; and back-crossing to TW419-052 three or more times in succession to produce selected fourth or higher backcross progeny plants that comprise said trait or locus. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox and other sites for site specific integration, which may also affect a desired trait if a functional nucleic acid is inserted at the integration site.

In addition, the above process and other similar processes described herein may be used to produce first generation progeny wheat seed by adding a step at the end of the process that comprises crossing TW419-052 with the introgressed trait or locus with a different wheat plant and harvesting the resultant first generation progeny wheat seed.

A further embodiment of the invention is a backcross conversion of wheat variety TW419-052. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in "Hybrid Wheat" by K. A. Lucken (pp. 444-452 In Wheat and Wheat Improvement, ed. Heyne, 1987). Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), powdery mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtlD). The trait of interest is transferred from the donor parent to the recurrent parent, in this case, the wheat plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Using TW419-052 to Develop Other Wheat Varieties

Wheat varieties such as TW419-052 are typically developed for use in seed and grain production. However, wheat varieties such as TW419-052 also provide a source of breeding material that may be used to develop new wheat varieties. Plant breeding techniques known in the art and used in a wheat plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of wheat varieties in a plant breeding program requires, in general, the development and evaluation of homozygous varieties. There are many analytical methods available to evaluate a new variety. The oldest and most traditional method of analysis is the observation of phenotypic traits but genotypic analysis may also be used.

The examples presented herein are provided for illustrative purposes only and not to limit the scope of any embodiment of the present invention.

EXAMPLES

Deposit of the wheat cultivar TW419-052 disclosed above and recited in the appended claims has been made with the American Type Culture Collection (ATCC), 10801 University Boulevard, Manassas, Va. 20110. The date of deposit was Mar. 18, 2013. All restrictions upon the deposit have been removed, and the deposit is intended to meet all of the requirements of 37 C.F.R. §1.801-1.809. The ATCC accession number for TW300-001 is PTA-122503. The deposit will be maintained in the depository for a period of 30 years, or 5 years after the last request, or for the effective life of the patent, whichever is longer, and will be replaced as necessary during that period.

Cultivar TW419-052 is a doubled-haploid (maize pollinator) soft red winter wheat developed from a cross made in 2002-2003. The $F_1$-derived doubled-haploid line was planted in a single nursery row (1 meter long) in the fall of 2004. It entered a single replicate observation trial in the fall of 2005 and remained in Ontario registration trials through 2010-2011. Thirteen of the 26 stations reported were from independent testers.

Cultivar TW419-052 is adapted to northeastern United States and eastern Canada, and TW419-052 has shown uniformity and stability for all traits. Cultivar TW419-052 is a doubled-haploid and self pollinated to ensure homozygosity and phenotypic stability. No variant traits have been observed or are expected in TW419-052. As described in Table 1, characteristics of cultivar TW419-052 are directly compared to several other soft red wheat cultivars that are well known in the North American wheat-production industry. Most of the data for the characteristics in Table 1 were derived from field plots where these cultivars were grown at the same time and locations so that any possible environmental effects on these specific characteristics were equivalent ("controlled") across cultivars.

TABLE 1

Morphology and Other Characteristics of TW419-052 Compared To Check Cultivars

| Characteristic | TW419-052 | Emmit | Branson |
|---|---|---|---|
| SEEDLING CHARACTERISTICS (4-leaf stage) | | | |
| Juvenile growth habit (Erect = 1, Semi-erect = 3, Intermediate = 5, Semi-prostrate = 7, Prostrate = 0) | 2-3 | 2 | 1-2 |
| Pubescence on sheaths of lower leaves (Glabrous = 1, Slightly Pubescent = 4, Strongly Pubescent = 7) | 1-2 | 1-2 | 1 |

TABLE 1-continued

Morphology and Other Characteristics of TW419-052 Compared To Check Cultivars

| Characteristic | TW419-052 | Emmit | Branson |
|---|---|---|---|
| Pubescence on blades of lower leaves (Glabrous = 1, Slightly Pubescent = 4, Strongly Pubescent = 7) | 1-2 | 1-2 | 1 |
| Color of lower leaf blade (Light Green = 1, Medium Green = 2, Dark Green = 3, Blue Green = 4) | 1-2 | 1 | 1-2 |
| Tillering capacity at low densities (Low = 1, High = 9) | 6 | 6 | 6-7 |
| FLAG-LEAF CHARACTERISTICS | | | |
| Color (Light Green = 1, Medium Green = 2, Dark Green = 3, Blue Green = 4) | 2-3 | 2-3 | 2-3 |
| Pubescence of blade (Glabrous = 1, Slightly Pubescent = 4, Strongly Pubescent = 7) | 1 | 1-2 | 1 |
| Waxiness of lower side of blade (Absent = 1, Slight = 5, Pronounced = 9) | 3 | 8 | 6 |
| Sheath waxy bloom (Absent = 1, Slight = 5, Pronounced = 9) | 5 | 6-7 | 7 |
| Sheath pubescence (Glabrous = 1, Slightly Pubescent = 4, Strongly Pubescent = 7) | 1 | 1 | 1 |
| Width (Narrow = 3, Medium = 5, Wide = 7) | 4 | 5 | 3 |
| Length (Short = 3, Medium = 5, Long = 7) | 6 | 5 | 5 |
| Curvature (Rectilinear = 1, Slightly Recurved = 3, Recurved = 5, Strongly Recurved = 7, Very Strongly Recurved = 9) | 1-2 | 3 | 2-3 |
| Attitude (Drooping = 3, Intermediate = 5, Upright = 7) | 4 | 7 | 3-4 |
| Auricles anthocyanin coloration (Absent = 1, Present = 9) | 1 | 1 | 1 |
| Auricles pubescence of margins (Glabrous = 1, Slightly Pubescent = 4, Strongly Pubescent = 7) | 1 | 5 | 1 |
| PLANT CHARACTERISTICS (after heading) | | | |
| Maturity (days to heading + 42) | 187 | 187 | 185 |
| Height (stem plus spike excluding awns, in inches) | 30.2 | 31.1 | 25.8 |
| Culm shape of neck at maturity (Straight = 1, Curved = 9) | 2 | 3.4 | 9 |
| Culm waxiness of upper internode (Absent = 1, Slight = 5, Pronounced = 9) | 1-2 | 4-5 | 4-5 |
| Culm pubescence of upper internode (Glabrous = 1, Slightly Pubescent = 4, Strongly Pubescent = 7) | 1 | 1 | 1 |
| Rachis pubescence of margins (Glabrous = 1, Slightly Pubescent = 4, Strongly Pubescent = 7) | 5-6 | 4 | 2-3 |
| Straw anthocyanin coloration at maturity (Absent = 1, Medium = 4, Strong = 7) | 1 | 1 | 1 |
| Straw pith (Hollow = 1, Thick Walled = 5, Solid = 9) | 1 | 1 | 2-3 |
| Stem color at maturity (White = 1, Yellow = 2, Brown = 3, Purple = 4, Other Specified = 5) | 2 | 2 | 1-2 |
| SPIKE CHARACTERISTICS | | | |
| Spike shape (Tapering = 1, Oblong = 2, Clavate = 3, Fusiform = 4, Other Specified = 5) | 1-2 | 1 | 1-2 |
| Spike attitude at maturity (Erect = 1, Inclined = 5, Nodding = 9) | 9 | 5 | 7 |
| Spike density (Lax = 3, Medium = 5, Dense = 7) | 5 | 5-6 | 5 |
| Spike length excluding awns, first tiller (Short = 3, Medium = 5, Long = 7) | 4 | 5 | 4 |
| Spike waxy bloom (Absent = 1, Slight = 5, Pronounced = 9) | 2-3 | 5-6 | 5 |
| Spike color at maturity (White = 1, Red to Brown = 2, Purple to Black = 3, Other Specified = 4) | 1 | 1 | 1 |
| Spike awnedness (Awnless = 1, Apically Awnletted = 2, Awnletted = 3, Awned = 4) | 2-3 | 2-3 | 3 |
| Awn length in relation to spike (NA, Shorter = 1, Equal = 2, Longer = 3) | 1 | 1 | 1 |
| Awn color (NA, White = 1, Light Brown = 2, Brown = 3, Black = 4) | 1 | 1 | 1 |
| Awn attitude (Appressed = 1, Spreading = 9) | 9 | 9 | 9 |
| Supernumerary spikelets (Absent = 1, Present = 2) | 1 | 1 | 1 |

TABLE 1-continued

Morphology and Other Characteristics of TW419-052 Compared To Check Cultivars

| Characteristic | TW419-052 | Emmit | Branson |
|---|---|---|---|
| GLUME CHARACTERISTICS | | | |
| Lower-glume width (Narrow = 3, Medium = 5, Wide = 7) | 6 | 5 | 4 |
| Lower-glume length (Short = 3, Medium = 5, Long = 7) | 5 | 5 | 6 |
| Lower-glume pubescence (Glabrous = 1, Slightly Pubescent = 4, Strongly Pubescent = 7) | 1-2 | 3-4 | 3-4 |
| Lower-glume shape of shoulder (wanting = 1, Oblique = 2, Rounded = 3, Square = 4, Elevated = 5, Apiculate = 6) | 2 | 2-4 | 4 |
| Lower-glume shoulder width (Narrow = 3, Medium = 5, Wide = 7) | 3 | 6 | 4 |
| Lower-glume shape of beak (Obtuse = 1, Acute = 2, Acuminate = 3) | 2 | 2-3 | 3 |
| Lower-glume beak length (Short = 3, Medium = 5, Long = 7) | 5 | 3-4 | 4 |
| Lower-glume internal imprint (Absent = 1, Small = 3, Medium = 5, Large = 7) | 6 | 5 | 6 |
| Chaff color at maturity (White = 1, Yellow = 2, Light Brown = 3, Brown = 4, Red = 5, Purple = 6, Other Specified = 7) | 1-2 | 1-2 | 2 |
| KERNEL CHARACTERISTICS | | | |
| Kernel type (Soft White = 1, Soft Red = 2, Hard White = 3, Hard Red = 4, Other Specified = 5) | 2 | 2 | 2 |
| Kernel color (White = 1, Light Red = 2, Medium Red = 3, Dark Red = 4, Amber = 5, Purple = 6, Other Specified = 7) | 3 | 2-3 | 2-3 |
| Kernel size (Small = 3, Medium = 5, Large = 7, Very Large = 9) | 5 | 6-7 | 7 |
| Kernel length (Short = 3, Medium = 5, Long = 7) | 4 | 5 | 6 |
| Kernel width (Narrow = 3, Medium = 5, Wide = 7) | 5 | 5 | 4 |
| Kernel weight (grams per 1000 kernels) | 34.4 | 39.2 | not tested |
| Kernel shape (Oval = 1, Ovate = 2, Elliptical = 3, Other Specified = 4) | 2 | 1-2 | 2 |
| Kernel cheek shape (Rounded = 1, Slightly Angular = 3, Angular = 5) | 1 | 1 | 1 |
| Kernel length of brush hairs (Short = 3, Medium = 5, Long = 7) | 5 | 7 | 4 |
| Kernel size of brush (Small = 3, Medium = 5, Large = 7) | 5 | 7 | 3 |
| Germ (embryo) shape (Round = 1, Oval = 2, Other Specified = 3) | 1-2 | 1 | 2 |
| Germ (embryo) size (Small = 3, Midsize = 5, Large = 7) | 5 | 5 | 4 |
| Kernel crease width (Narrow = 3, Midwide = 5, Wide = 7) | 3 | 6 | 3 |
| Kernel crease depth (Shallow = 1, Mid-deep = 2, Deep = 3, Pitted = 4, Other Specified = 5) | 1 | 1-2 | 1-2 |
| AGRONOMIC CHARACTERISTICS | | | |
| Winter survival (Poor = 3, Fair = 5, Good = 7) | 7 | 7 | 7 |
| Pre-harvest sprouting (Not Tested = 0, Low = 3, Medium = 5, High = 7) | 3 | 3 | 3 |
| REACTION TO DISEASE (Resistant = 1, Moderately Resistant = 3, Tolerant = 5, Moderately Susceptible = 7, Susceptible = 9) | | | |
| *Septoria tritici* leaf blotch | 2.0 | 2.5 | 2.8 |
| Powdery mildew | 2.2 | 3.1 | not tested |
| Leaf rust | 4.0 | 4.5 | 2.8 |
| Barley yellow dwarf virus | 0.5 | 1.1 | 0.2 |
| Deoxynivalenol (DON) (parts per million in grain) | 3.6 | 5.4 | not tested |
| *Fusarium* head blight (percentage overall infection) | 23.8 | 32.4 | not tested |
| QUALITY CHARACTERISTICS | | | |
| Bread quality (NA = 0, Poor = 3, Fair = 5, Good = 7) | 0 | 0 | 0 |
| Pastry and biscuit quality (NA = 0, Poor = 3, Fair = 5, Good = 7) | 6 | 5 | 6 |
| Macaroni quality (NA = 0, Poor = 3, Fair = 5, Good = 7) | 0 | 0 | 0 |

Cultivar TW419-052 is 9.6% higher yielding than the mean of the checks (Superior and Emmit) over 25 station-years, 2006-2011. Cultivar TW419-052 out-yielded the mean of the checks, Emmit and Superior, over the 25 station-years of testing by 3.1% and 17%, respectively. Cultivar TW419-052 out-yielded both checks in 15 of the 25 stations used for yield (Table 2). Cultivar TW419-052 was heavier than the checks for test weight and slightly worse than the checks for lodging (Table 2).

TABLE 2

Yield, Test Weight, and Lodging of Cultivar TW419-052 Compared to Check Cultivars Over 5 Years (2006-2011)

| | Number of Locations | | |
|---|---|---|---|
| | 25 | 23 | 8 |
| | Yield | Grain Test Weight (lb/Winchester | Lodging |
| Cultivars | (kg/ha)[1] | bu)[2] | (0 to 9) |
| TW419-052 | 5736 | 58.8 | 0.8 |
| Superior | 4903 | 56.3 | 0.4 |
| Emmit | 5566 | 56.9 | 0.1 |
| Check Mean | 5234 | 56.6 | 0.3 |

[1]kilogram/hectare × 0.88 = bushels/acre
[2](pound/Winchester bushel × 1.292) + 1.419 = kilogram/hectoliter Cultivar TW419-052 is similar to the check cultivar Superior in kernel characteristics except it has smaller kernels as evident by the lighter 1000 kernel weight (Table 3).

TABLE 3

Kernel (Grain) Characteristics of Cultivar TW419-052 Compared to a Check Cultivar Over 2 Years (2009-2011) and Total of 9 Locations

| Cultivars | Test Weight (lb/ Winchester bu)[1] | Kernel Weight (g/1000 kernels) | Kernel Hardness (Index: −20 to 120) | Grain Protein (%) | Falling Number (seconds) |
|---|---|---|---|---|---|
| TW419-052 | 59.6 | 35.3 | 78.1 | 9.65 | 331 |
| Superior | 58.3 | 37.7 | 74.8 | 9.94 | 267 |

[1](pound/Winchester bushel × 1.292) + 1.419 = kilogram/hectoliter

Flour produced from the grain of TW419-052 has excellent biscuit and pastry applications, comparable to those of the cultivar Superior (Table 4).

TABLE 4

Flour Characteristics of Cultivar TW419-052 Compared to a Check Cultivar Over 2 Years (2009-2011) and Total of 9 Locations

| Cultivars | Flour Yield (%) | Flour Ash (%) | Flour Protein (%) | Protein Difference[1] (%) | Cookie Spread (cm) | Cookie W/T[2] |
|---|---|---|---|---|---|---|
| TW419-052 | 79.0 | 0.41 | 8.42 | 1.24 | 8.52 | 11.27 |
| Superior | 76.6 | 0.48 | 8.83 | 1.11 | 8.42 | 11.04 |

[1]Difference between grain and flour protein contents.
[2]Cookie width to thickness ratio.

In summary, wheat cultivar TW419-052 is a soft red winter wheat adapted to northeastern United States and eastern Canada. TW419-052 is noted for its high grain yield, good test weight, and good resistance to a variety of fungal diseases, while meeting industry standards for other agronomic, grain, and baking characteristics.

The foregoing invention has been described in detail by way of illustration and example for purposes of clarity and understanding. However, it will be obvious that certain changes and modifications such as single locus modifications and mutations, somoclonal variants, variant individuals selected from large populations of the plants of the instant variety and the like may be practiced within the scope of the invention.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

What is claimed is:

1. A seed of soft red winter wheat cultivar designated TW419-052, representative seed of said variety having been deposited under ATCC Accession No. PTA13626.

2. A wheat plant, or part thereof, produced by growing the seed of claim 1.

3. A tissue culture of regenerable cells produced from the plant of claim 2.

4. A protoplast produced from the tissue culture cells of claim 3.

5. The tissue culture of claim 3, wherein the cells of the tissue culture are from a plant part selected from the group consisting of meristematic tissue, anthers, leaves, embryos, pollen, kernel, head, stem, root, root tip, ovule, and flower.

6. A wheat plant regenerated from the tissue culture cells of claim 3, said plant having all the morphological and physiological characteristics of wheat variety TW419-052.

7. Grain harvested from the plant claim 2.

8. A grain product produced from grain harvested from claim 7.

9. A method for producing an F1 wheat seed, comprising crossing the plant of claim 2, with a different wheat plant and harvesting the resulting F1 wheat seed.

10. A method of producing a male-sterile wheat plant comprising transforming the wheat plant of claim 2, with a nucleic acid molecule that confers male sterility.

11. A method of producing an herbicide-resistant, insect-resistant, or abiotic-stress-tolerant wheat plant comprising transforming the wheat plant of claim 2, with a transgene that confers herbicide resistance, insect resistance, disease or abiotic stress tolerance.

12. An herbicide-resistant wheat plant produced by the method of claim 11.

13. An insect-resistant wheat plant produced by the method of claim 11.

14. An abiotic-stress-tolerant wheat plant produced by the method of claim 11.

15. The wheat plant of claim 11, wherein the transgene encodes a Bacillus thuringiensis endotoxin.

16. A method of producing a wheat plant with modified fatty acid metabolism, modified protein metabolism or modified carbohydrate metabolism comprising transforming the wheat plant of claim 2 with a transgene encoding a polypeptide selected from the group consisting of modified glutenins, gliadins, stearyl-ACP-desaturase, fructosyltransferase, levansucrase, alpha-amylase, invertase and starch branching enzyme.

17. A method of introducing a desired trait into wheat variety TW419-052 comprising: (a) crossing TW419-052 plants grown from TW419-052 seed, representative seed of which has been deposited under ATCC Accession No:

PTA-13626, with plants of another wheat line that comprise a desired trait to produce $F_1$ progeny plants, wherein the desired trait is selected from the group consisting of male sterility, herbicide resistance, insect resistance, disease resistance and waxy starch; (b) selecting $F_1$ progeny plants that have the desired trait to produce selected $F_1$ progeny plants; (c) crossing the selected progeny plants with the TW419-052 plants to produce backcross progeny plants; (d) selecting for backcross progeny plants that have the desired trait and physiological and morphological characteristics of wheat variety TW419-052 to produce selected backcross progeny plants; and (e) repeating steps (c) and (d) three or more times in succession to produce selected fourth or higher backcross progeny plants that comprise the desired trait and all of the physiological and morphological characteristics of wheat variety TW419-052.

18. A wheat plant produced by the method of claim 17, wherein the plant has the desired trait and all of the physiological and morphological characteristics of wheat cultivar TW419-052.

19. A disease resistant wheat plant produced by the method of claim 17.

* * * * *